US011406836B1

(12) United States Patent
O'Driscoll et al.

(10) Patent No.: US 11,406,836 B1
(45) Date of Patent: Aug. 9, 2022

(54) WIRELESS POWER RECEIVER COIL FOR NEUROMODULATION DEVICE (71) Applicant: Verily Life Sciences LLC, South San Francisco, CA (US)

(72) Inventors: Stephen O'Driscoll, San Francisco, CA (US); Damiano Patron, San Bruno, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 46 days.

(21) Appl. No.: 16/553,866

(22) Filed: Aug. 28, 2019

Related U.S. Application Data (60) Provisional application No. 62/730,104, filed on Sep. 12, 2018.

(51) Int. Cl.
| | |
|---|---|
| *A61N 1/37* | (2006.01) |
| *A61N 1/378* | (2006.01) |
| *A61N 1/36* | (2006.01) |
| *H01F 38/14* | (2006.01) |
| *H02J 50/12* | (2016.01) |

(52) U.S. Cl.
CPC ......... *A61N 1/3787* (2013.01); *A61N 1/3605* (2013.01); *H01F 38/14* (2013.01); *H02J 50/12* (2016.02)

(58) Field of Classification Search
CPC .... A61N 1/3787; A61N 1/3605; H01F 38/14; H02J 50/12
See application file for complete search history.

(56) References Cited

U.S. PATENT DOCUMENTS

| | | | | |
|---|---|---|---|---|
| 6,137,237 A | * | 10/2000 | MacLennan | H05B 41/24 315/248 |
| 8,847,548 B2 | | 9/2014 | Kesler et al. | |
| 8,907,531 B2 | | 12/2014 | Hall et al. | |

(Continued)

FOREIGN PATENT DOCUMENTS

| | | |
|---|---|---|
| CN | 106468474 | 3/2017 |
| CN | 207587110 | 7/2018 |
| EP | 3096337 | 11/2016 |

OTHER PUBLICATIONS

Johns et al., "Designing a Qi-compliant receiver coil for wireless power systems, Part 1", Analog Applications Journal, 2012, pp. 8-14.

(Continued)

*Primary Examiner* — Amanda K Hulbert
*Assistant Examiner* — Natasha Patel
(74) *Attorney, Agent, or Firm* — Kilpatrick Townsend & Stockton LLP (57) ABSTRACT

The present disclosure relates to implantable neuromodulation devices, and in particular to a wireless power coil in a low profile environment such as with a neurostimulator. Particularly, aspects of the present disclosure are directed to a medical device that comprises a lossy housing surrounding a power supply, and a receiving coil configured to exchange power wirelessly via a wireless power transfer signal and deliver the power to the power supply. The receiving coil is adjacent the lossy housing. The receiving coil is a helical structure with a total rise that is less than or equal to a height of the lossy housing.

8 Claims, 6 Drawing Sheets

(56) References Cited

U.S. PATENT DOCUMENTS

| | | | |
|---|---|---|---|
| 2005/0075697 A1* | 4/2005 | Olson | A61N 1/3787 |
| | | | 607/61 |
| 2008/0294207 A1 | 11/2008 | Kast et al. | |
| 2011/0193688 A1 | 8/2011 | Forsell | |
| 2012/0235501 A1* | 9/2012 | Kesler | H02J 7/025 |
| | | | 307/104 |
| 2012/0235634 A1* | 9/2012 | Hall | H02J 50/50 |
| | | | 320/108 |
| 2014/0265621 A1 | 9/2014 | Wong et al. | |
| 2016/0197511 A1* | 7/2016 | Atasoy | H02J 50/10 |
| | | | 307/104 |
| 2018/0262053 A1* | 9/2018 | Corum | H04B 13/02 |

OTHER PUBLICATIONS

Khan et al., "Wireless Transfer of Powerto Low Power Implanted Biomedical Devices: Coil Design Considerations", IEEE International Instrumentation and Measurement Technology Conference Proceedings, May 13-16, 2012, abstract, 1 page.

Johns et al., "Designing a Qi-compliant receiver coil for wireless power systems, Part 1", Analog Applications Journal, 2012, 9 pages.

Khan et al., "Wireless Transfer of Powerto Low Power Implanted Biomedical Devices: Coil Design Considerations", IEEE International Instrumentation and Measurement Technology Conference Proceedings, May 13-16, 2012.

U.S. Appl. No. 16/508,628, Non-Final Office Action, dated Jul. 12, 2021, 13 pages.

* cited by examiner

WIRELESS POWER RECEIVER COIL FOR NEUROMODULATION DEVICE

CROSS-REFERENCE TO RELATED APPLICATIONS

The present application claims priority and benefit from U.S. Provisional Application No. 62/730,104, filed Sep. 12, 2018, entitled "WIRELESS POWER RECEIVER COIL FOR NEUROMODULATION DEVICE", the entire contents of which are incorporated herein by reference for all purposes.

FIELD OF THE INVENTION

The present disclosure relates to implantable neuromodulation devices, and in particular to a wireless power coil in a low profile environment such as with a neurostimulator.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically comprise an implant device including a neurostimulator having electronics connected to a lead assembly that delivers electrical pulses to electrodes interfaced with nerves or nerve bundles via an electrode assembly. In order to supply energy to the neurostimulator an energy source such as an electrochemical cell or a battery is typically arranged in the neurostimulator (e.g., within the housing of the neurostimulator). However, electrochemical cells and batteries have a limited life time. After the electrochemical cell or battery has been emptied or discharged, it has to be re-charged or replaced when the energy stored is not sufficient for the physiological treatment. In the case of an implanted device such as a neurostimulator it is for several reasons preferred to recharge an electrochemical cell or battery rather than replacing the cell or battery. One reason is the invasive nature associated with removal and replacement of the energy source and the risk to the patient. Other reasons include that some implanted devices consume a relatively large amount of energy and would then have to have their energy sources replaced relatively often, which can be inconvenient and costly for the patient.

One of the non-invasive methods to recharge the electrochemical cell or battery is through wireless power transfer. This method comprises an external power charger and a power receiver embedded into the implant device. The power receiver is typically made by a coil of wire connected to power management circuitry. However, in the case of implant devices meant for both subcutaneous and deeper point applications, the implant devices are typically characterized by a very low thickness profile. Given the very low thickness profile of the implant devices, the coil is often placed next to other components such as metal enclosures for electronic circuitry, which reduce the wireless power transfer efficiency. Thus, wasting energy, requiring longer charge times and/or more frequent charging sessions. In view of these inefficiencies, it is desirable to develop neuromodulation devices and systems that are capable of having design flexibility, and desirable mechanical properties to increase the wireless power transfer efficiency.

BRIEF SUMMARY

In various embodiments, a medical device is provided comprising: a lossy housing surrounding a power supply; and a receiving coil configured to exchange power wirelessly via a wireless power transfer signal and deliver the power to the power supply. The receiving coil is adjacent the lossy housing, and the receiving coil is a helical structure with a total rise that is less than or equal to a height of the lossy housing.

In some embodiments, the helical structure is three-dimensional and the total rise is determined based on a shape, a number of turns, a pitch of each turn, a helix length, a helix angle, or a combination thereof. In some embodiments, the total rise is substantially the same as the height of the lossy housing. In some embodiments, the receiving coil comprises wound wire formed from conductive material, and the conductive material is comprised of gold (Au), gold/chromium (Au/Cr), platinum (Pt), platinum/iridium (Pt/Ir), titanium (Ti), gold/titanium (Au/Ti), or any alloy thereof.

In some embodiments, receiving coil is within 4 mm of the lossy housing, and the lossy housing is made of a material capable of causing attenuation or dissipation of the wireless power transfer signal.

In some embodiments, the receiving coil is spaced a predetermined distance from the lossy housing such that, during the exchange of power, a coupling factor between the receiving coil and a transmitting coil is greater than 0.5.

In various embodiments, a medical device is provided comprising: a housing; power supply within the housing and connected to an electronics module; and a receiving coil configured to exchange power wirelessly via a wireless power transfer signal and deliver the power to the power supply. In some embodiments, the receiving coil is a helical structure with a height that is determined based on a pitch between each of a plurality of turns, and at least one pitch of a turn of the plurality of turns is different from a remainder of turns of the plurality of turns.

In some embodiments, the height is determined based on: (i) a first pitch between a first turn and a second turn of the receiving coil; (ii) a second pitch between a last turn and a second to last turn of the receiving coil; and (iii) a third pitch between remaining turns between the second turn and the second to last turn, and wherein the at least one pitch is the first pitch or the second pitch.

In some embodiments, the first pitch and the second pitch are less than the third pitch.

In some embodiments, the first pitch is the same as the second pitch.

In some embodiments, the height is determined based on: (i) a first pitch between a first turn and a second turn of the receiving coil; (ii) a second pitch between a last turn and a second to last turn of the receiving coil; and (iii) a third pitch between a majority of turns between the second turn and the second to last turn, and wherein the at least one pitch is the first pitch or the second pitch.

In some embodiments, the first pitch is the same as the second pitch.

In some embodiments, the first pitch and the second pitch are less than the third pitch.

In some embodiments, the helical structure has a shape of a rounded rectangle and includes from 4 to 15 turns.

In some embodiments, the height of the helical structure is less than or equal to a height of the lossy housing.

In various embodiments, neuromodulation system is provided comprising: a transmitting conductive structure configured to exchange power wirelessly via a wireless power transfer signal; an implantable neurostimulator including: a lossy housing; a connector attached to a hole in the lossy housing; one or more feedthroughs that pass through the connector; an electronics module within the lossy housing and connected to the one or more feedthroughs; a power supply within the lossy housing and connected to the electronics module; and a receiving conductive structure disposed outside of the housing and connected to the power supply, wherein the receiving conductive structure is configured to exchange power wirelessly with the transmitting conductive structure via the wireless power transfer signal and deliver the power to the power supply. The receiving conductive structure is adjacent the lossy housing, and the receiving conductive structure is a helical structure with a total rise that is less than or equal to a height of the lossy housing, and a lead assembly including: a lead body including a conductor material; a lead connector that connects the conductor material to the one or more feedthroughs; and one or more electrodes connected to the conductor material.

In some embodiments, the total rise is determined based on a pitch between each of a plurality of turns, and wherein at least one pitch of a turn of the plurality of turns is different from a remainder of turns of the plurality of turns.

In some embodiments, the total rise is determined based on: (i) a first pitch between a first turn and a second turn of the receiving coil; (ii) a second pitch between a last turn and a second to last turn of the receiving coil; and (iii) a third pitch between remaining turns between the second turn and the second to last turn, and wherein the at least one pitch is the first pitch or the second pitch.

In some embodiments, the total rise is determined based on a helical angle between each of a plurality of turns, and wherein at least one helical angle of a turn of the plurality of turns is different from a remainder of helical angles of the plurality of turns.

In some embodiments, the total rise is determined based on: (i) a first helical angle between a first turn and a second turn of the receiving coil; (ii) a second helical angle between a last turn and a second to last turn of the receiving coil; and (iii) a third helical angle between remaining turns between the second turn and the second to last turn, and wherein the at least one helical angle is the first helical angle or the second helical angle.

In various embodiments, a medical device is provided that includes: a lossy housing surrounding a power supply; and a receiving coil configured to exchange power wirelessly via a wireless power transfer signal and deliver the power to the power supply The receiving coil is spaced a predetermined distance from the lossy housing; and the predetermined distance is determined based on: (i) a size constraint of the medical device, (ii) an area of the receiving coil, and (iii) a coupling factor between the receiving coil and a transmitting coil of greater than 0.5.

In some embodiments, the size constraint of the medical device includes a width of less than 24 mm, a height of less than 15 mm, and a length of less than 80 mm. In some embodiments, the medical device further includes a connector attached to an electronics module through a hole in the lossy housing, and the area of the receiving coil is determined based on: (i) the size constraint of the medical device, (ii) a width of the lossy housing, (iii) a length of the connector, and (iv) the coupling factor between the receiving coil and the transmitting coil of greater than 0.5.

In some embodiments, the receiving coil has a quality factor of greater than 50. In some embodiments, the receiving coil has a quality factor of greater than 100.

In some embodiments, the receiving coil is comprised gold (Au), gold/chromium (Au/Cr), platinum (Pt), platinum/iridium (Pt/Ir), titanium (Ti), gold/titanium (Au/Ti), or any alloy thereof. In some embodiments, housing is comprised of metal. Optionally, the metal is titanium or an alloy thereof.

In some embodiments, the predetermined distance is from 250 μm to 6 mm.

In some embodiments, the receiving coil has a height that is determined based on: (i) a first pitch between a first turn and a second turn of the receiving coil; (ii) a second pitch between a last turn and a second to last turn of the receiving coil; (iii) a third pitch between remaining turns between the second turn and the second to last turn, and (iv) a height of the medical device. In some embodiments, the receiving coil has a width that is determined based on: (i) a width of the medical device; (ii) a width of the lossy housing, and (iii) the predetermined distance.

In some embodiments, the medical device further includes a connector attached to an electronics module through a hole in the lossy housing. The receiving coil has a length that may be determined based on: (i) a length of the medical device; and (ii) a length of the connector. In some embodiments, the area of the receiving coil is determined based on: (i) the height of the receiving coil, (ii) the width of the receiving coil, (iii) the length of the receiving coil, and (iv) the coupling factor between the receiving coil and the transmitting coil of greater than 0.5.

In various embodiments, a medical device is provided that includes: a housing; power supply within the housing and connected to an electronics module; and a receiving coil configured to exchange power wirelessly via a wireless power transfer signal and deliver the power to the power supply. The receiving coil is a helical structure with a height that is determined based on: (i) a first pitch between a first turn and a second turn of the receiving coil; (ii) a second pitch between a last turn and a second to last turn of the receiving coil; and (iii) a third pitch between remaining turns between the second turn and the second to last turn, and the first pitch and the second pitch are less than the third pitch.

In some embodiments, the medical device has a height of less than 15 mm, and the height of the receiving coil is determined based on: (i) the first pitch between the first turn and the second turn of the receiving coil; (ii) the second pitch between the last turn and the second to last turn of the receiving coil; (iii) the third pitch between remaining turns between the second turn and the second to last turn; and (iv) the height of the medical device. In some embodiments, the height of the receiving coil is less than or equal to the height of the medical device. In some embodiments, the first pitch is from 10 μm to 3 mm, the second pitch is from 10 μm to 3 mm, and the third pitch is from 500 μm to 1 cm. In some embodiments, the first pitch is the same as the second pitch. In some embodiments, the helical structure has a shape of a rounded rectangle and includes from 4 to 15 turns.

In some embodiments, the receiving coil is spaced a predetermined distance from the housing, and wherein the predetermined distance is determined based on: (i) a size constraint of the medical device, (ii) an area of the receiving coil, and (iii) a coupling factor between the receiving coil and a transmitting coil of greater than 0.5.

In various embodiments, a wireless power transfer system is provided that includes: a transmitting conductive structure configured to exchange power wirelessly via a wireless power transfer signal; and a receiving conductive structure integrated into a lossy environment comprising a lossy component The receiving conductive structure is configured to exchange power wirelessly with the transmitting conductive structure via the wireless power transfer signal. Additionally, the receiving conductive structure is spaced a predetermined distance from the lossy component; and the predetermined distance is determined based on: (i) a size constraint of the lossy environment, (ii) an area of the receiving coil, and (iii) a coupling factor between the receiving coil and a transmitting coil of greater than 0.5.

In some embodiments, the transmitting conductive structure and the receiving conductive structure have a quality factor of greater than 50. In some embodiments, the transmitting conductive structure and the receiving conductive structure have a quality factor of greater than 100.

In some embodiments, the transmitting conductive structure and the receiving conductive structure are comprised of gold (Au), gold/chromium (Au/Cr), platinum (Pt), platinum/iridium (Pt/Ir), titanium (Ti), gold/titanium (Au/Ti), or any alloy thereof. In some embodiments, the lossy component is comprised of metal. Optionally, the metal is titanium or an alloy thereof.

In some embodiments, the predetermined distance is from 250 μm to 6 mm.

In some embodiments, the receiving conductive structure is a helical structure with a height that is determined based on: (i) a first pitch between a first turn and a second turn of the helical structure; (ii) a second pitch between a last turn and a second to last turn of the helical structure; (iii) a third pitch between remaining turns between the second turn and the second to last turn, and (iv) a height of the lossy environment. In some embodiments, the receiving conductive structure has a width that is determined based on: (i) a width of the lossy environment; (ii) a width of the lossy component; and (iii) the predetermined distance.

In some embodiments, the medical device further includes a connector attached to an electronics module through a hole in the lossy component. The receiving conductive structure has a length that may be determined based on: (i) a length of the lossy environment; and (ii) a length of the connector. In some embodiments, the area of the receiving conductive structure is determined based on: (i) the height of the receiving conductive structure, (ii) the width of the receiving conductive structure, (iii) the length of the receiving conductive structure, and (iv) the coupling factor between the receiving conductive structure and the transmitting conductive structure of greater than 0.5.

In various embodiments, a neuromodulation system is provided that includes: a transmitting conductive structure configured to exchange power wirelessly via a wireless power transfer signal; an implantable neurostimulator including: a lossy housing; a connector attached to a hole in the lossy housing; one or more feedthroughs that pass through the connector; an electronics module within the lossy housing and connected to the one or more feedthroughs; a power supply within the lossy housing and connected to the electronics module; and a receiving conductive structure disposed outside of the housing and connected to the power supply. The receiving conductive structure is configured to exchange power wirelessly with the transmitting conductive structure via the wireless power transfer signal and deliver the power to the power supply, the receiving conductive structure is spaced a predetermined distance from the lossy housing; and the predetermined distance is determined based on: (i) a size constraint of the implantable neurostimulator, (ii) an area of the receiving conductive structure, and (iii) a coupling factor between the receiving conductive structure and the transmitting conductive structure of greater than 0.5. The neuromodulation system may further include a lead assembly including: a lead body including a conductor material; a lead connector that connects the conductor material to the one or more feedthroughs; and one or more electrodes connected to the conductor material.

In some embodiments, the size constraint of the implantable neurostimulator includes a width of less than 24 mm, a height of less than 15 mm, and a length of less than 80 mm. In some embodiments, the area of the receiving conductive structure is determined based on: (i) the size constraint of the implantable neurostimulator, (ii) a width of the lossy housing, (iii) a length of the connector, and (iv) the coupling factor between the receiving coil and the transmitting coil of greater than 0.5.

In some embodiments, the transmitting conductive structure and the receiving conductive structure have a quality factor of greater than 50. In some embodiments, the transmitting conductive structure and the receiving conductive structure have a quality factor of greater than 100.

In some embodiments, the transmitting conductive structure and the receiving conductive structure are comprised of gold (Au), gold/chromium (Au/Cr), platinum (Pt), platinum/iridium (Pt/Ir), titanium (Ti), gold/titanium (Au/Ti), or any alloy thereof. In some embodiments, the lossy housing is comprised of metal. Optionally, the metal is titanium or an alloy thereof.

In some embodiments, the predetermined distance is from 250 μm to 6 mm.

In some embodiments, the receiving conductive structure is a helical structure with a height that is determined based on: (i) a first pitch between a first turn and a second turn of the helical structure; (ii) a second pitch between a last turn and a second to last turn of the helical structure; (iii) a third pitch between remaining turns between the second turn and the second to last turn, and (iv) a height of the implantable neurostimulator. In some embodiments, the receiving conductive structure has a width that is determined based on: (i) a width of the implantable neurostimulator; (ii) a width of the lossy housing, and (iii) the predetermined distance. In some embodiments, the receiving conductive structure has a length that is determined based on: (i) a length of the implantable neurostimulator; and (ii) a length of the connector. In some embodiments, the area of the receiving conductive structure is determined based on: (i) the height of the receiving conductive structure, (ii) the width of the receiving conductive structure, (iii) the length of the receiving conductive structure, and (iv) the coupling factor between the receiving conductive structure and the transmitting conductive structure of greater than 0.5.

BRIEF DESCRIPTION OF THE DRAWINGS

The present invention will be better understood in view of the following non-limiting figures, in which.

DETAILED DESCRIPTION

I. Introduction

The following disclosure describes a wireless power coil in a low profile environment such as with a neurostimulator. The basic principle of an inductively coupled power transfer system includes a transmitter coil and a receiver coil. Both coils form a system of magnetically coupled inductors. An alternating current in the transmitter coil generates a magnetic field which induces a voltage in the receiver coil. By attaching a load to the receiver coil the voltage can be used to power an electronic device or charge a battery. The magnetic field generated by the transmitter coil radiates (approximately equally) in all directions, hence the flux drops rapidly with distance (obeying an inverse square law). Consequently, the receiver coil must be placed as close as possible to the transmitter coil (less than 10 mm) to intercept the most flux. This requirement of a close proximity between the transmitter coil and the receiver coils is not always practical for neuromodulation therapy, especially instances in which the neurostimulator is implanted deeper than the subcutaneous layer (e.g., within the brain or thoracic cavity).

Alternative, wireless charging systems have been developed that transfer power between a transmitter coil and a receiver coil that are operating at identical resonant frequencies (determined by the coils' distributed capacitance, resistance and inductance). The basic premise is that the energy "tunnels" from one coil to the other instead of radiating in all directions from the primary coil; and thus resonant wireless charging is not governed by the inverse square law. This technique is still "inductive" in that the oscillating magnetic field generated by the transmitter coil induces a current in the receiver coil and takes advantage of the strong coupling that occurs between resonant coils even when separated by tens of centimeters. Resonant wireless charging addresses the main drawbacks of inductive wireless charging, which is the requirement to closely couple the coils and the demand for precise alignment from the user. However, resonant wireless charging is not without its own drawbacks. A primary drawback is a relatively low efficiency due to flux leakage (even at close range a well-designed system might demonstrate an efficiency of 30% at 2 cm, dropping to 15% at 75 cm coil separation, greater circuit complexity and, because of the (typically) high operating frequencies, potential electromagnetic interference (EMI) challenges.

The efficiency of the power transfer in resonant wireless charging depends on the energy coupling rate between the coils and the characteristic parameters for each coil (i.e., inductor). The amount of inductive coupling between coils is measured by their mutual inductance. The strength of the coupling may be expressed as a coupling factor, which is determined by the area of the coils including the distance between the coils, the ratio of width of the receiver coil/width of the transmitter coil, the shape of the coils and the angle between the coils. The characteristic parameters for each coil includes the resonance frequency and the intrinsic loss rate of the coils. A quality factor measures how well the system stores energy and is expressed as the ratio of the resonance frequency matching between the coils and the intrinsic loss rate of the coils. A higher quality factor indicates a lower rate of energy loss relative to the stored energy of the coils; the oscillations die out more slowly. Resonance allows the wireless power transfer system to operate at greater distances compared to a non-resonant one. However, frequency mismatch may be observed, which has the effect of limiting the maximum power stored and thus transferred. One factor that may influence the coupling factor and the quality factor of the coils is the external environment near the coils. In particular, the close proximity of an environmental factor such as metal or tissue has been found to greatly influence the efficiency of the wireless power transfer system.

Most conventional wireless power transfer systems involve transferring power between a transmitting coil and a receiving coil in free space without nearby environmental factors. Consequently, the best possible efficiency of most conventional wireless power transmission systems depends on the coupling factor between the coils and the quality factors. However, for a low profile implanted device meant for subcutaneous and deeper applications, the various components of the neurostimulator are packed into a tight volume of space. In a low profile implanted device, this means that the receiving coil will likely be placed next to a number of environmental factors including the metal enclosure, which has been found to influence the coupling (e.g., reduce the energy available to the receiving coil due to energy absorption and change of field shape) and the quality factor of the coils (e.g., create a frequency mismatch).

To address these limitations and problems, it has been discovered that to improve efficiency of the wireless power transfer in a system with environmental factors it is important to maintain sufficient spacing between the coils and the environmental factors. Given a fixed area or volume for the implantable device, maximizing the coil area to maintain sufficient coupling and keeping enough spacing to avoid the influence from the environmental factors means that it is important to find a tradeoff between these requirements. One illustrative embodiment of the present disclosure is directed to a medical device that comprises a lossy housing surrounding a power supply; and a receiving coil configured to exchange power wirelessly via a wireless power transfer signal and deliver the power to the power supply. The receiving coil is spaced a predetermined distance from the lossy housing. The predetermined distance is determined based on: (i) a size constraint of the medical device, (ii) an area of the receiving coil, and (iii) a coupling factor between the receiving coil and a transmitting coil of greater than 0.5.

In other embodiments, a medical device is provided comprising: a housing; power supply within the housing and connected to an electronics module; and a receiving coil configured to exchange power wirelessly via a wireless power transfer signal and deliver the power to the power supply. The receiving coil is a helical structure with a height that is determined based on: (i) a first pitch between a first turn and a second turn of the receiving coil; (ii) a second pitch between a last turn and a second to last turn of the receiving coil; and (iii) a third pitch between remaining turns between the second turn and the second to last turn. The first pitch and the second pitch are less than the third pitch.

In other embodiments, a wireless power transfer system is provided comprising a transmitting conductive structure configured to exchange power wirelessly via a wireless power transfer signal; and a receiving conductive structure integrated into a lossy environment comprising a lossy component. The receiving conductive structure is configured to exchange power wirelessly with the transmitting conductive structure via the wireless power transfer signal. The receiving conductive structure is spaced a predetermined distance from the lossy component. The predetermined distance is determined based on: (i) a size constraint of the lossy environment, (ii) an area of the receiving coil, and (iii) a coupling factor between the receiving coil and a transmitting coil of greater than 0.5.

In other embodiments, a neuromodulation system is provided comprising a transmitting conductive structure configured to exchange power wirelessly via a wireless power transfer signal; an implantable neurostimulator including: a lossy housing; a connector attached to a hole in the lossy housing; one or more feedthroughs that pass through the connector; an electronics module within the lossy housing and connected to the one or more feedthroughs; a power supply within the lossy housing and connected to the electronics module; and a receiving conductive structure disposed outside of the housing and connected to the power supply. The receiving conductive structure is configured to exchange power wirelessly with the transmitting conductive structure via the wireless power transfer signal and deliver the power to the power supply. The receiving conductive structure is spaced a predetermined distance from the lossy housing, and the predetermined distance is determined based on: (i) a size constraint of the implantable neurostimulator, (ii) an area of the receiving conductive structure, and (iii) a coupling factor between the receiving conductive structure and the transmitting conductive structure of greater than 0.5. The neuromodulation system further comprises a lead assembly including: a lead body including a conductor material; a lead connector that connects the conductor material to the one or more feedthroughs; and one or more electrodes connected to the conductor material.

Advantageously, these approaches provide a neuromodulation system, which has a very low thickness profile, an efficient wireless power transfer, and greater design flexibility. More specifically, these approaches enable for spacing between the wireless power receiving coil and environmental factors presented by the neuromodulation system while also maximizing the area of the wireless power receiving coil in order to maximize the wireless power transfer into the implanted neurostimulator.

II. Neuromodulation Devices and Systems with Wireless Power Transfer

Figure 1:
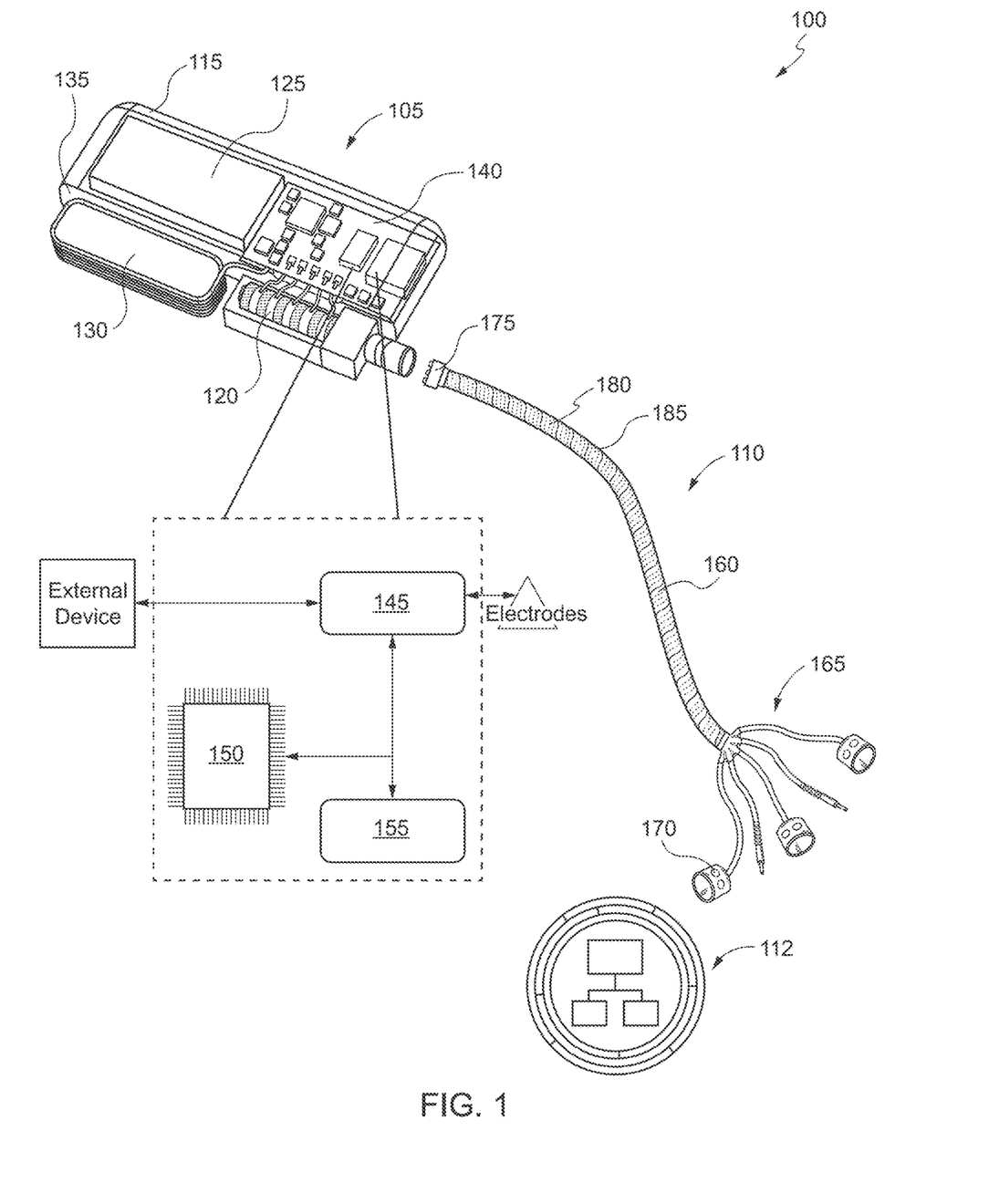
FIG. 1 shows an shows a neuromodulation system in accordance with various embodiments.

FIG. 1 shows a neuromodulation system 100 in accordance with some aspects of the present invention. In various embodiments, the neuromodulation system 100 includes an implantable neurostimulator 105, a lead assembly 110, and a transmitting conductive structure 112 (e.g., a transmitting coil). The implantable neurostimulator 105 may include a housing 115, a connector 120, a power source 125, a receiving conductive structure 130 (e.g., a wireless power coil or a receiving coil), an antenna 135, and an electronics module 140 (e.g., a computing system). The housing 115 may be comprised of materials that are biocompatible such as bioceramics or bioglasses for radio frequency transparency, or metals such as titanium or alloys thereof. In accordance with various aspects, the size and shape of the housing 115 is selected such that the neurostimulator 105 can be implanted within a patient. In the example shown in FIG. 1, the connector 120 is attached to a hole in a surface of the housing 115 such that the housing 115 is hermetically sealed. The connector 120 may include one or more feedthroughs (i.e., electrically conductive elements, pins, wires, tabs, pads, etc.) mounted within a header and extending through the surface of the header from an interior to an exterior of the header. The power source 125 (e.g., a battery) may be within the housing 115 and connected (e.g., electrically connected) to the electronics module 140 to power and operate the components of the electronics module 140. In some embodiments, the power source 125 and the electronics module 140 are surrounded by the housing 115. The wireless power coil 130 may be outside the housing 115 and configured to receive electrical energy from the charging device 112. In some embodiments, the wireless power coil 130 is attached to an outside surface of the housing 115 by a spacer 142. The wireless power coil 130 is connected (e.g., electrically connected) to the power source 125 to provide the electrical energy to recharge or supply power to the power source. The antenna 135 may be outside the housing 115 and connected (e.g., electrically connected) to the electronics module 140 for wireless communication with external devices via, for example, radiofrequency (RF) telemetry.

In some embodiments, the electronics module 140 may be connected (e.g., electrically connected) to interior ends of the connector 120 such that the electronics module 140 is able to apply a signal or electrical current to conductive traces of the lead assembly 110 connected to exterior ends of the connector 120. The electronics module 140 may include discrete and/or integrated electronic circuit components that implement analog and/or digital circuits capable of producing the functions attributed to the neuromodulation devices or systems such as applying or delivering neural stimulation to a patient. In various embodiments, the electronics module 140 may include software and/or electronic circuit components such as a pulse generator 145 that generates a signal to deliver a voltage, current, optical, or ultrasonic stimulation to a nerve or artery/nerve plexus via electrodes, a controller 150 that determines or senses electrical activity and physiological responses via the electrodes and sensors, controls stimulation parameters of the pulse generator 145 (e.g., control stimulation parameters based on feedback from the physiological responses), and/or causes delivery of the stimulation via the pulse generator 145 and electrodes, and a memory 155 with program instructions operable on by the pulse generator 145 and the controller 150 to perform one or more processes for applying or delivering neural stimulation.

In various embodiments, the lead assembly 110 is a monolithic structure that includes a cable or lead body 160. In some embodiments, the lead assembly 110 further includes one or more electrode assemblies 165 having one or more electrodes 170, and optionally one or more sensors. In some embodiments, the lead assembly 110 further includes a lead connector 175. In certain embodiments, the lead connector 175 is bonding material that bonds conductor material of the lead body 160 to the electronics module 140 of the implantable neurostimulator 105 via the connector 120. The bonding material may be a conductive epoxy or a metallic solder or weld such as platinum. In other embodiments, the lead connector 175 is conductive wire, conductive traces, or bond pads (e.g., a wire, trace, or bond pads formed of a conductive material such as copper, silver, or gold) formed on a substrate and bonds a conductor of the lead body 160 to the electronics module 140 of the implantable neurostimulator 105. In alternative embodiments, the implantable neurostimulator 105 and the lead body 160 are designed to connect with one another via a mechanical connector 175 such as a pin and sleeve connector, snap and lock connector, flexible printed circuit connectors, or other means known to those of ordinary skill in the art.

The conductor material of the lead body 160 may be one or more conductive traces 180 formed on a supporting structure 185. The one or more conductive traces 180 allow for electrical coupling of the electronics module 140 to the electrodes 170 and/or sensors of the electrode assemblies 165. The supporting structure 185 may be formed with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends may be used. The conductive material for the traces 180 may be any suitable conductor such as stainless steel, silver, copper or other conductive materials, which may have separate coatings or sheathing for anticorrosive, insulative and/or protective reasons.

The electrode assemblies 165 may include the electrodes 170 and/or sensors fabricated using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). In various embodiments, the electrode assemblies 165 include a base material that provides support for microelectronic structures including the electrodes 170, a wiring layer, optional contacts, etc. In some embodiments, the base material is the supporting structure 185. The wiring layer may be embedded within or located on a surface of the supporting structure 185. The wiring layer may be used to electrically connect the electrodes 170 with the one or more conductive traces 180 directly or indirectly via a lead conductor. The term "directly", as used herein, may be defined as being without something in between. The term "indirectly", as used herein, may be defined as having something in between. In some embodiments, the electrodes 170 may make electrical contact with the wiring layer by using the contacts.

III. Wireless Power Transfer System

Figure 2:
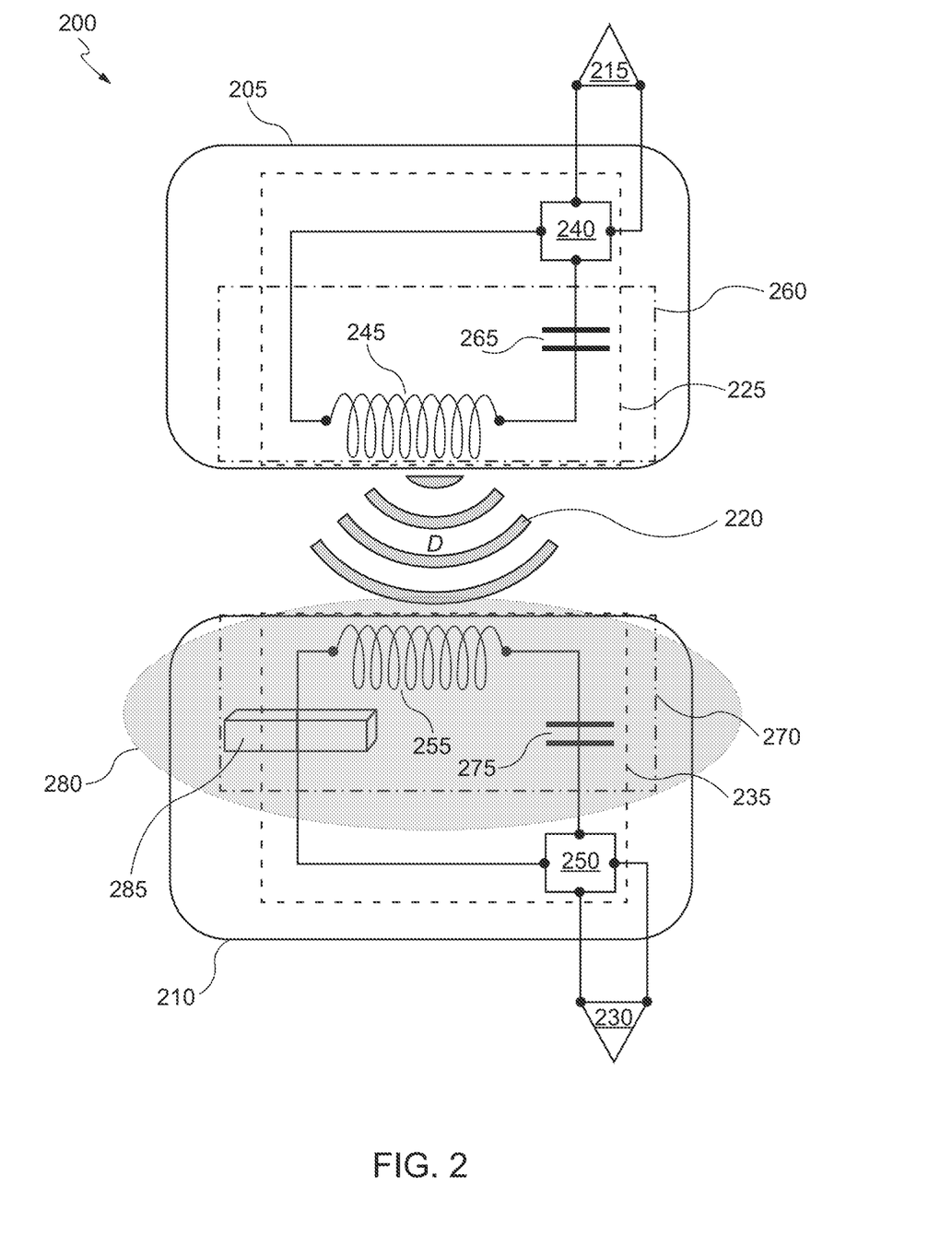
FIG. 2 shows a wireless power transfer system in accordance with various embodiments.

FIG. 2 shows a wireless power transfer system 200 comprising a transmitting device 205 and a receiving device 210 spaced apart from one another by a distance (D). In some embodiments, the transmitting device 205 is connected to a power supply 215 such a main power line. The transmitting device 205 is configured to convert input power (DC or AC electric current) from the power supply 215 into a wireless power transfer signal 220. For example, the input power is converted into the wireless power transfer signal 220 by a first coupling device 225. In some embodiments, the wireless power transfer signal 220 is a time varying electromagnetic field. The receiving device 210 is configured to receive the wireless power transfer signal 220, convert the wireless power transfer signal 220 into an output power (AC or DC electric current), and deliver the output power to a load 230 (e.g., the power source 125 described with respect to FIG. 1). For example, the wireless power transfer signal 220 is converted into the output power by a second coupling device 235. Accordingly, the second coupling device 235 is configured to exchange power wirelessly with the first coupling device 225 via the wireless power transfer signal 220.

In some embodiments, the first coupling device 225 includes an optional oscillator 240 and a transmitting conductive structure 245 (e.g., a transmitting conductive structure 112 described with respect to FIG. 1). In some embodiments, the transmitting conductive structure 245 is a transfer coil of wire configured to exchange power wirelessly via the wireless power transfer signal 220. The oscillator 240 may be used to generate a high frequency AC current, which drives the transmitting conductive structure 245 to generate the wireless power transfer signal 220 such as the time varying or oscillating electromagnetic field. In some embodiments, the second coupling device 235 includes an optional rectifier 250 and a receiving conductive structure 255 (e.g., a receiving conductive structure 130 described with respect to FIG. 1). In some embodiments, the receiving conductive structure 255 is a receiving coil of wire configured to exchange power wirelessly with the transmitting conductive structure 245 via the wireless power transfer signal 220. The rectifier 250 may be used to convert the AC current induced at the receiving conductive structure 255 into DC current, which is delivered to the load 235. In some embodiments, the transmitting conductive structure 245 and the receiving conductive structure 255 have a quality factor of greater than 50. In other embodiments, the transmitting conductive structure 245 and the receiving conductive structure 255 have a quality factor of greater than 100.

In some embodiments, the first coupling device 225 further includes a resonant circuit 260 which includes: (i) the transmitting conductive structure 245 connected to a capacitor 265, (ii) the transmitting conductive structure 245 being a self-resonant coil; or (iii) another resonator (not shown) with internal capacitance. In some embodiments, the second coupling device 235 further includes a resonant circuit 270 which includes: (i) the receiving conductive structure 255 connected to a capacitor 275, (ii) the receiving conductive structure 255 being a self-resonant coil; or (iii) another resonator (not shown) with internal capacitance. The first coupling device 225 and the second coupling device 235 are tuned to resonate at a same resonant frequency. The resonance between the transmitting conductive structure 245 and the receiving conductive structure 255 may increase coupling and more efficient power transfer.

In various embodiments, the receiving conductive structure 255 is in a lossy environment 280. As used herein "lossy" means having or involving the dissipation of electrical or electromagnetic energy. A "lossy" environment is thus characterized as an environment causing the attenuation or dissipation of electrical energy. In some embodiments, the lossy environment 280 includes one or more lossy environmental factors or components 285, which result in current loss during the wireless power transfer between the transmitting conductive structure 245 and the receiving conductive structure 255. In some embodiments, the lossy environment 280 is an implantable medical device such as a neurostimulator as described with respect to FIG. 1. In some embodiments, the one or more lossy environmental factors or components 285 include body fluid, body tissue, a lossy component of the implantable medical device, or a combination thereof. In some embodiments, the lossy component of the medical device is a housing made of a material capable of causing attenuation or dissipation of a wireless power transfer signal. In some embodiments, the material is a metal. In certain embodiments, the metal is titanium or an alloy thereof.

IV. Wireless Power Coil

Figure 3A:
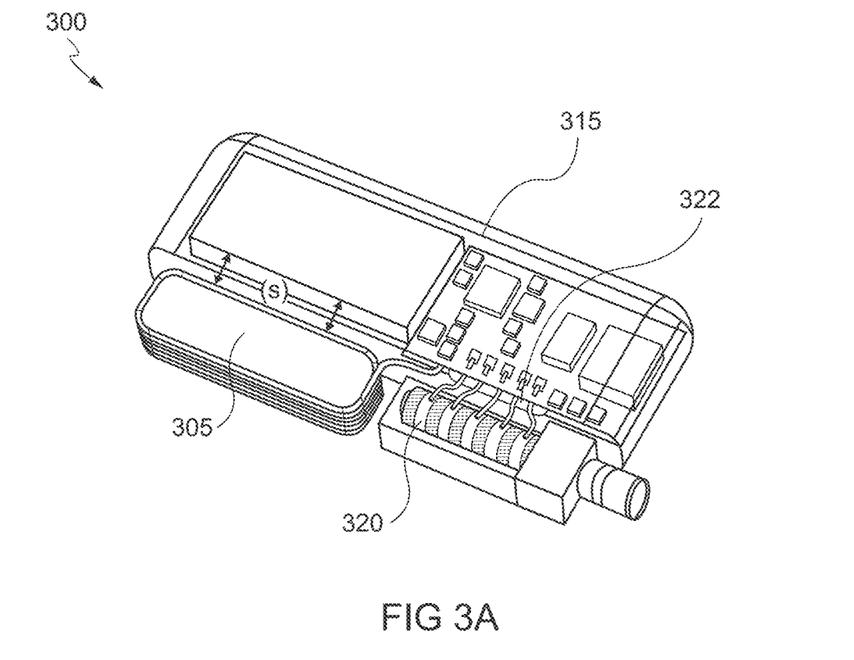
FIGS. 3A-3F show a neurostimulator with a wireless power receiver coil in accordance with various embodiments.
Figure 3B:
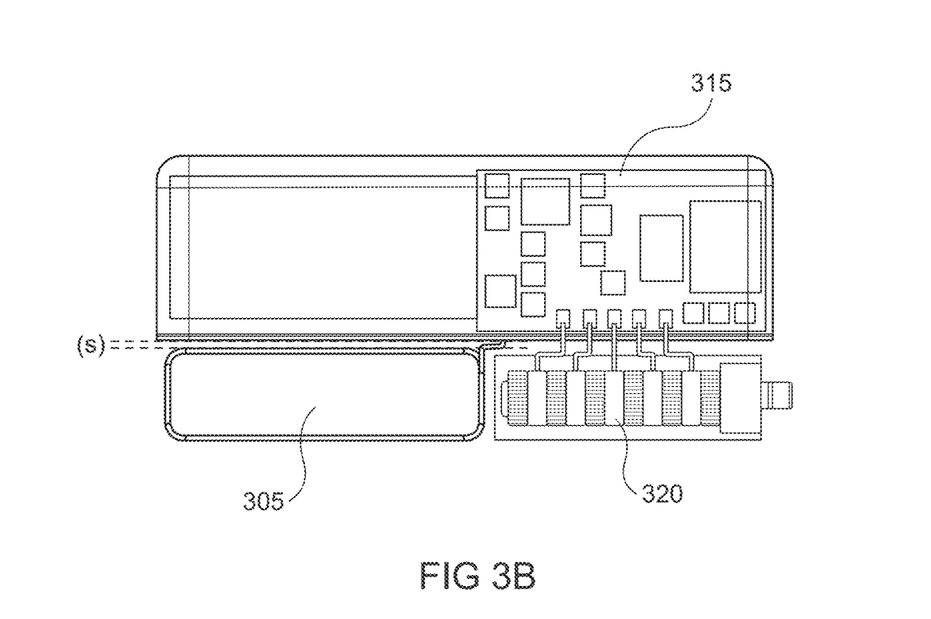
Figure 3C:
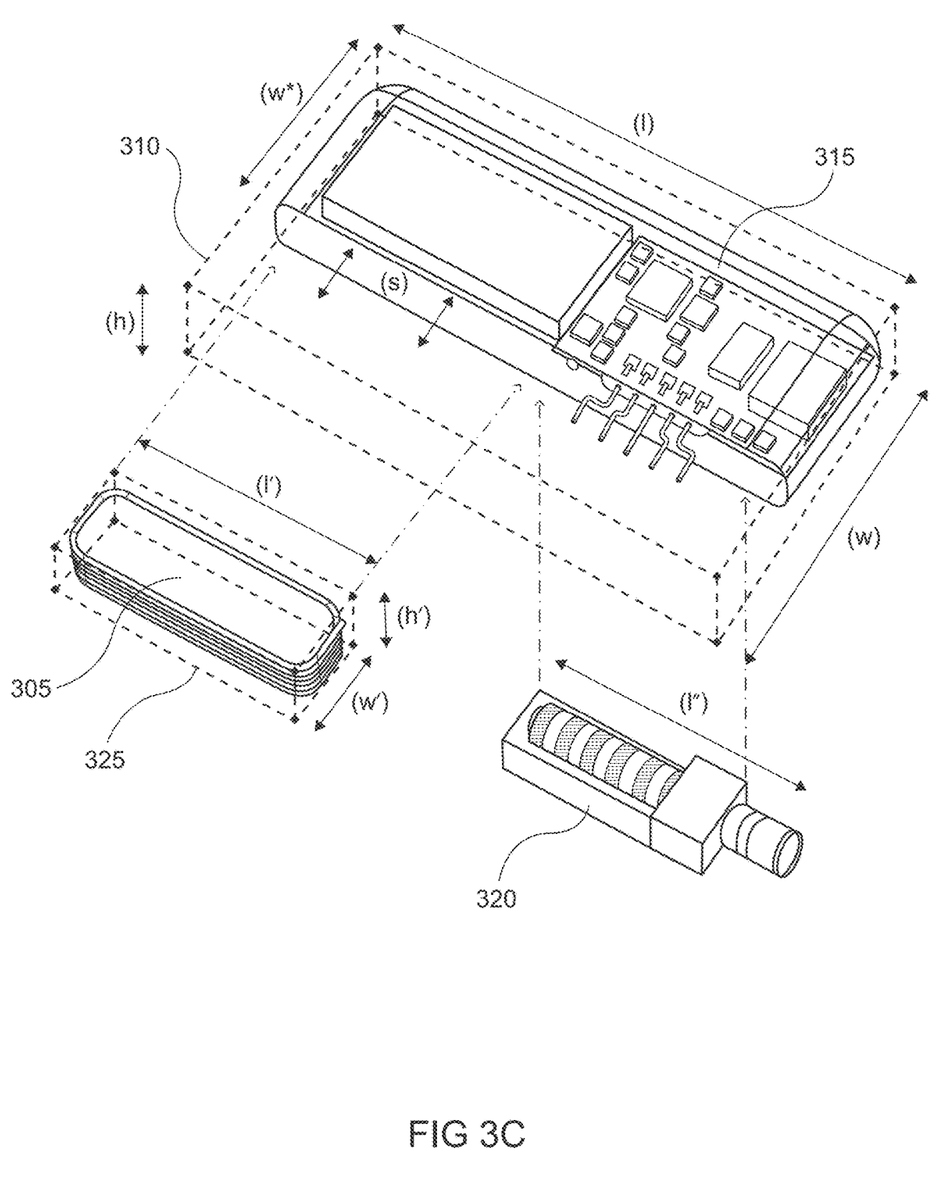

FIGS. 3A, 3B, and 3C show an implantable device 300 (e.g., the implantable neurostimulator 105 described with respect to FIG. 1) comprising a receiving conductive structure 305 (e.g., the receiving conductive structure 255 described with respect to FIG. 2) in accordance with aspects of the present disclosure. In various embodiments, a size of the implantable device 300 is constrained small enough such that the device can be implanted in a less complex and minimally invasive manner, for example, through a trocar or cannula. In some embodiments, the implantable device 300 has a size constraint 310 including: (i) a width (w) of less than 24 mm, for example from 10 mm to 20 mm, (ii) a height (h) of less than 15 mm, for example from 5 mm to 13 mm, and (iii) a length (l) of less than 80 mm, for example from 20 mm to 40 mm. In some embodiments, the size constraint further includes a cross sectional area of less than 190 $mm^2$, for example from 75 $mm^2$ to 160 $mm^2$. In some embodiments, the size constraint further includes a total volume of less than 28,800 $mm^3$, for example from 10,000 $mm^3$ to 20,000 $mm^3$.

In various embodiments, the receiving conductive structure 305 is physically configured to exchange power wirelessly via a wireless power transfer signal and deliver the power to the power supply. Physically configured means the receiving conductive structure 305 includes: (i) inductance and power receiving capability to meet the needs of the implantable device 200 including the ability to transfer power to the power source with at least an 8% overall efficiency; (ii) the mechanical dimensions (e.g., the height, width and length of the receiving conductive structure 305) fit to the size constraint 310 of the implantable device 300; (iii) the receiving conductive structure 305 is spaced apart from environmental factors to sufficiently avoid coupling of power to the environmental factors; and (iv) the receiving conductive structure 305 is biocompatible and a durable construction for the implanted environment.

In some embodiments, the receiving conductive structure 305 is a receiving coil comprising wound wire. In certain embodiments, the wire is formed from a conductive material. The conductive material may be comprised of various metals or alloys thereof, for example, gold (Au), gold/chromium (Au/Cr), platinum (Pt), platinum/iridium (Pt/Ir), titanium (Ti), gold/titanium (Au/Ti), or any alloy thereof. In some embodiments, the coil has an inductance ranging from 0.5 uH to 50 uH or from 1 uH to 15 uH, for example about 1.1 uH. In some embodiments, the coil has a working frequency ranging from 1 mHz to 100 mHz or from 3 mHz to 25 mHz, for example about 6.78 mHz (ISM Standard Frequency). In some embodiments, the coil has a working voltage ranging from 5 V to 50 V or from 10 V to 35 V, for example about 25 V. In some embodiments, the wire of the coil has an American Wire Gauge (AWG) ranging from 25 AWG to 40 AWG or from 28 AWG to 37 AWG, for example 32 AWG. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

FIGS. 3A, 3B, and 3C show the implantable device 300 may further comprise a lossy housing 315 and optionally a connector 320 attached to an electronics module through a hole 322 in the lossy housing 315 (e.g., the housing 115 and connector 120 described with respect to FIG. 1). In various embodiments, an epoxy covers at least a portion of the implantable device 300 in order to hold the components together and protect the components from environmental factors such as biological fluid. The epoxy may be a resin comprising one or more low molecular weight pre-polymers, one or more higher molecular weight polymers, or combinations thereof, which comprise at least two epoxide groups. In some embodiments, the epoxy covers substantially, if not entirely, the entire device 300 (e.g., the receiving conductive structure 305, the lossy housing 315, and the connector 320 are covered). In other embodiments, the epoxy covers select components of the device 300 but not all of the components (e.g., at least the receiving conductive structure 305 and the connector 320 are covered while the lossy housing is exposed). In some embodiments, the lossy housing 315 is comprised of materials that are biocompatible such as bioceramics or bioglasses for radio frequency transparency, or metals such as titanium or an alloy thereof.

In various embodiments, the conductive structure 305 is adjacent to the lossy housing 315. The term "adjacent" as used herein means that one structure is next door to, abutting, close to, near to, next to, by, close by, by the side of, bordering (on), beside, alongside, abreast of, contiguous with, proximate to, attached to, touching, or joining another structure. In some embodiments, close to, near to, next to, by, close by, by the side of, means that the conductive structure 305 is spaced or within a predetermined distance (s) from the lossy housing 315. As described herein, the lossy housing 310 may be an environmental factor that may influence performance of the receiving conductive structure 305 and thus the performance of the wireless power transfer system. In order to minimize the influence of the lossy housing 315 on the performance of the receiving conductive structure 305, the receiving conductive structure 305 is spaced a predetermined distance (s) from the lossy housing 315. However, the predetermined distance (s) is not boundless as in free space, and instead the predetermined distance (s) is bounded by one or more factors including the size constraint 310 of the implantable device 300, the area 325 of the receiving conductive structure 305, a requirement to minimize coupling of power from the receiving conductive structure 305 to the housing 310, and a requirement to limit a shift in the resonance frequency or decrease in the quality factor of the receiving conductive structure 305. In some embodiments, the predetermined distance (s) is determined based on: (i) the size constraint 310 of the implantable device 300, (ii) the area 325 of the receiving conductive structure 305, and (iii) a coupling factor between the receiving conductive structure 305 and the transmitting conductive structure of greater than 0.5. In some embodiments, the predetermined distance (s) is selected such that the conductive structure 305 is within 4 mm of the lossy housing 315. In some embodiments, the predetermined distance (s) is less than or equal to 4 mm, from 250 μm to 4 mm, or from 500 μm to 3 mm, for example about 1 mm. As used herein, when an action is "triggered by" or "based on" something, this means the action is triggered or based at least in part on at least a part of the something.

FIG. 3C shows that determining the predetermined distance (s) involves a tradeoff between increasing the predetermined distance (s), which minimizes coupling of power from the receiving conductive structure 305 to the lossy housing 315, while maintaining a sufficient area 325 for the receiving conductive structure 305 in the size constraint 310 of the implantable device 300 to ultimately achieve a coupling factor between the receiving conductive structure 305 and the transmitting conductive structure of greater than 0.5. The coupling factor is generally determined by the distance (D) between the receiving conductive structure 305 and the transmitting conductive structure and the area 325 encompassed by the receiving conductive structure 305 and the transmitting conductive structure. For example, the greater the amount of the wireless power transfer signal (e.g., the greater the amount of flux from the magnetic field) that reaches the receiving conductive structure 305, the better the conductive structures are coupled and the higher the coupling factor. The amount of the wireless power transfer signal that reaches the receiving conductor structure 305 may be increased by increasing the area 325 of the receiving conductor structure 305. However, the coupling factor may be decreased by the presence of an environmental factor such as the housing 310, which may couple with the receiving conductive structure 305 and leach power that is being transferred to the receiving conductive structure 305.

As shown in FIG. 3C, the implantable device 300 has a size constraint 310. In some embodiments, the size constraint 310 includes: (i) a width (w) of less than 24 mm, for example from 10 mm to 20 mm, (ii) a height (h) of less than 15 mm, for example from 5 mm to 13 mm, and (iii) a length (l) of less than 80 mm, for example from 20 mm to 40 mm. In certain embodiments, the size constraint 310 includes a width of less than 24 mm, a height of less than 15 mm, and a length of less than 80 mm. The receiving conductor structure 305 has area 325 defined by (w')×(h')×(l'). In some embodiments, the area 325 of the receiving conductor structure 305 is determined based on: (i) the size constraint 310 of the implantable device 300, (ii) a width (w*) of the lossy housing 315, (iii) optionally the length (l") of the connector 320, and (iv) the coupling factor between the receiving conductor structure 305 and the transmitting conductor structure of greater than 0.5. In some embodiments, the width (w') is determined based on: (i) the width (w) of the implantable device 300; (ii) the width (w*) of the lossy housing 320, and (iii) the predetermined distance (s). In some embodiments, the length (l") is determined based on: (i) a length (l) of the implantable device 300; and (ii) a length (l") of the connector 320. In some embodiments, the height (h') is determined based on: (i) the height (h) of the implantable device 300. Accordingly, one dimension of the transmitting conductor structure 305 that is not determined by more than the size constraint 310 of the implantable device 300 is the height (h').

Figure 3D:
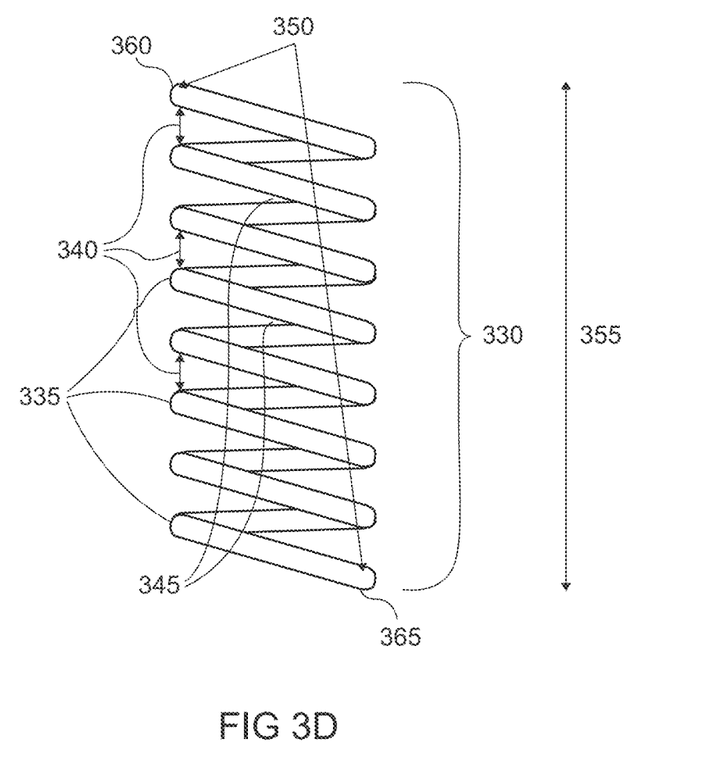

In order to increase the maximum possible area 325 of the receiving conductor structure 305 to maintain the coupling factor between the receiving conductor structure 305 and the transmitting conductor structure of greater than 0.5 while also accommodating for the predetermined distance (s), the height (h') of the receiving conductor structure 305 may be adjusted in a vertical direction. In various embodiments, in order to increase the maximum possible area 325, the receiving conductor structure 305 is formed in a three-dimensional manner rather than the conventional two-dimensional or planar coil. Testing has revealed that a three-dimensional coil is capable of maintaining sufficient coupling (i.e., the coupling factor between the receiving conductor structure 305 and the transmitting conductor structure of greater than 0.5) and power transfer with the transmitting conductor structure in such an enlarged area. In some embodiments, the receiving conductor structure 305 is a three dimensional spiral or helix, as shown in FIG. 3D.

Figure 3E:
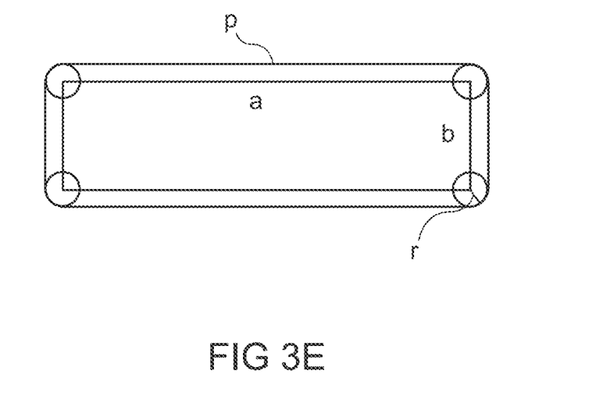

The helix includes characteristics designed to maximize the area 325 of the receiving conductor structure 305 in view of: (i) the size constraint 310 of the implantable device 300, (ii) a width (w*) of the lossy housing 315, (iii) optionally the length (l") of the connector 320, and (iv) the coupling factor between the receiving conductor structure 305 and the transmitting conductor structure of greater than 0.5. In some embodiments, the characteristics of the helix include a shape 330, a number of turns 335, a pitch 340 (rise of the helix for one turn), a helix angle 345, a helix length 350 (a length of the coil), a total rise 355 of the helix (overall coil height (h')), or combinations thereof. In some embodiments, the shape 330 of the coil is rounded rectangular. As used herein, the term "rounded rectangle" means a shape obtained by taking the convex surface of four equal circles of radius r and placing their centers at the four corners of a rectangle with side lengths a and b and creating a perimeter p around the surface of the four equal circles and the rectangle, where the perimeter p of the shape is equal to $2(a+b+\pi r)$, as shown in FIG. 3E. While the rounded rectangle shape of the coil is described herein in particular detail with respect to several described embodiments, it should be understood that other shapes of the coil have been contemplated without departing from the spirit and scope of the present invention. For example, the shape of the coil may be square, rectangular, circular, or round, etc.

In some embodiments, the helix has a plurality of turns. In some embodiments, the helix has greater than 4 turns or from 4 to 30 turns or from 4 to 15 turns, for example 9 turns, and a pitch between each of the turns from 10 μm to 1 cm or from 250 μm to 2 mm, for example about 500 μm. In some embodiments, the pitch between turns is the same or different. In some embodiments, the helix angle is from 5° to 85°, from 5° to 45°, or from 7° to 25°, for example, about 20°. In some embodiments, the helix length is from 2 cm to 100 cm or 25 cm to 75 cm, e.g., about 50 cm, from a first end 360 to a second end 365. In some embodiments, the total rise or overall coil height (h') is less than 15 mm, for example from 5 mm to 13 mm.

Figure 3F:
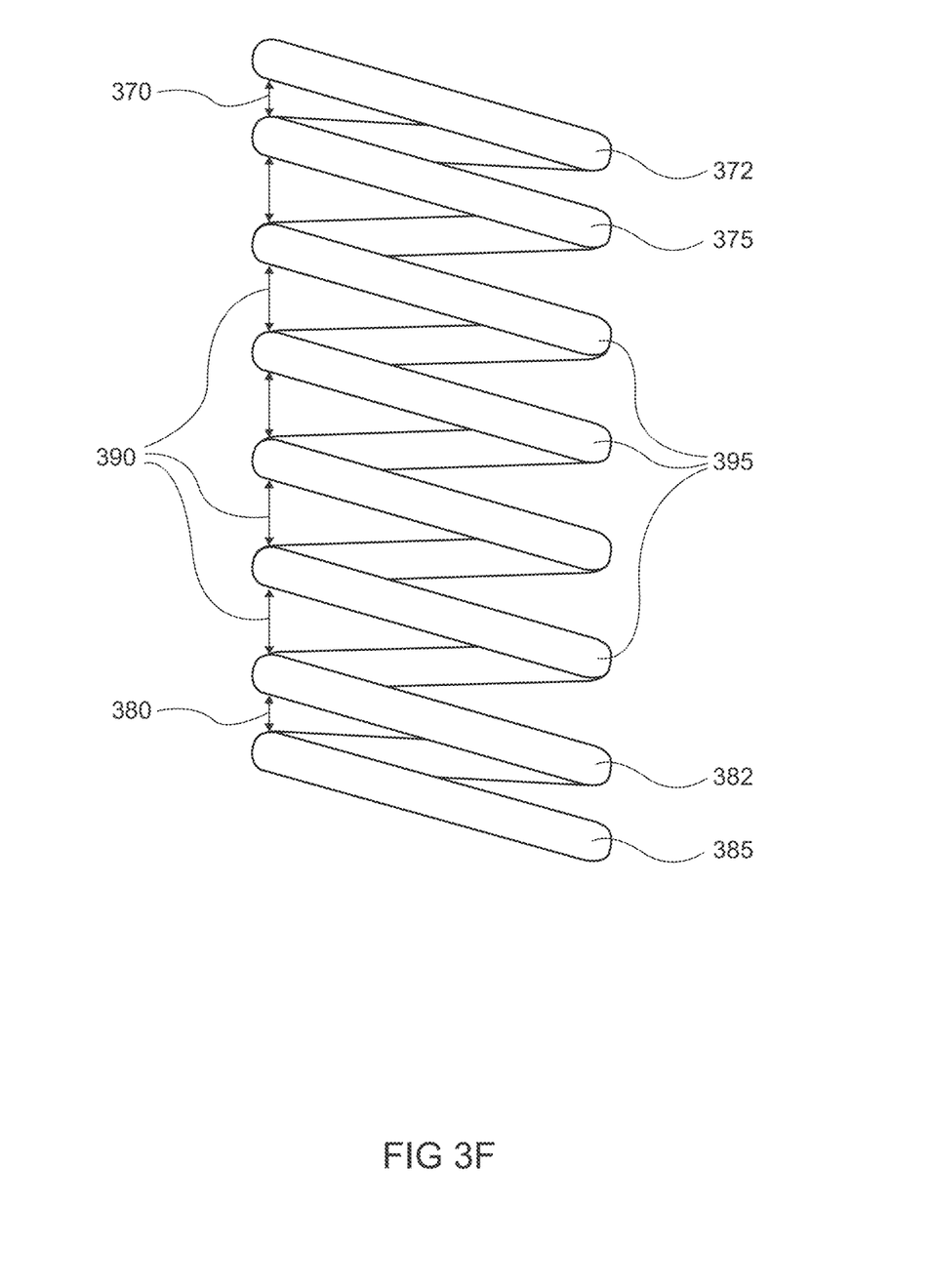

In various embodiments, the number of turns 335 and the helix length 350 are increased to maximize the area 320 occupied by the receiving conductive structure 305. In some embodiments, the number of turns 335 and the helix length 350 are increased by adjusting the pitch 340, the helix angle 345, and the total rise 355. In some embodiments, as shown in FIG. 3F, the receiving conductor structure 305 is a helical structure with a total rise 355 or height (h') that is determined based on a pitch between each of a plurality of turns. In some embodiments, the height (h') of the helical structure is substantially the same as a height of the lossy housing (e.g., height (h) of the size constraint). In some embodiments, the height (h') of the helical structure is less than or equal to the lossy housing (e.g., height (h) of the size constraint). In some embodiments, at least one pitch (e.g., pitch 370) of a turn (e.g., turn 372) of the plurality of turns is different from a remainder of turns of the plurality of turns. In some embodiments, a pitch (e.g., pitch 370) between a first turn 372 and a second turn 375 of the plurality of turns and a pitch (e.g., pitch 380) between a last turn 382 and a second to last turn 385 of the plurality of turns are the same pitch but less than a pitch (e.g., pitch 390) for a majority of turns (more than 50% of the turns between the given points) between the second turn and the second to last turn. In some embodiments, the height (h') is determined based on (i) a first pitch 370 between a first turn 372 and a second turn 375 of the receiving conductor structure 305; (ii) a second pitch 380 between a last turn 382 and a second to last turn 385 of the receiving conductor structure 305; and (iii) a third pitch 390 between remaining turns 395 between the second turn 375 and the second to last turn 385. In certain embodiments, the first pitch 370 and/or the second pitch 380 are the same. In certain embodiments, the first pitch 370 and/or the second pitch 380 is different from the third pitch 390. In certain embodiments, the first pitch 370 and the second pitch 380 are less than the third pitch 390.

In some embodiments, the total rise or height (h') is determined based on a helical angle between each of a plurality of turns. In some embodiments, at least one helical angle of a turn of the plurality of turns is different from a remainder of helical angles of the plurality of turns. In some embodiments, a helical angle between a first turn 372 and a second turn 375 of the plurality of turns and a helical angle between a last turn 382 and a second to last turn 385 of the plurality of turns are the same helical angle but less than a helical angle for a majority of turns (more than 50% of the turns between the given points) between the second turn and the second to last turn. In some embodiments, the height (h') is determined based on (i) a first helical angle between a first turn 372 and a second turn 375 of the receiving conductor structure 305; (ii) a second helical angle 380 between a last turn 382 and a second to last turn 385 of the receiving conductor structure 305; and (iii) a third helical angle 390 between remaining turns 395 between the second turn 375 and the second to last turn 385. In certain embodiments, the first helical angle and/or the second helical angle are the same. In certain embodiments, the first helical angle and/or the second helical angle is different from the third helical angle. In certain embodiments, the first helical angle and the second helical angle are less than the third helical angle.

The total rise 355 or height (h') may be determined further based on the size constraint 310 of the implantable device 300, in particular, the height (h) of the implantable device 300. For example, the total rise 355 or height (h') of the receiving conductor structure 305 may be determined to be less than or equal to the height (h) of the implantable device 300. In some embodiments, the first pitch 370 and the second pitch 380 are from 10 μm to 3 mm or from 250 μm to 2 mm, for example about 500 μm; and the third pitch 390 is from 500 μm to 1 cm or from 1 mm to 3 mm, for example about 2 mm. In some embodiments, the first pitch 370 and the second pitch 380 are less than the third pitch 390. In some embodiments, the first pitch 370 is the same as the second pitch 380. In other embodiments, the first pitch 370 is different from the second pitch 380.

Accordingly, by increasing the total rise 355 or height (h') of the receiving conductive structure 305 and decreasing the first pitch 370 and the second pitch 380 it is possible to increase the number of turns 335 and the helix length 350 of the receiving conductive structure 305 to maximize the area 320 occupied by the receiving conductive structure 305 while maintaining the sizing constraint 310 for the implantable device 300 and the predetermined distance (s) between the lossy housing 315 and the receiving conductive structure 305.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:
1. A medical device comprising:
a lossy housing surrounding a power supply; and
a receiving coil configured to exchange power wirelessly via a wireless power transfer signal and deliver the power to the power supply,
wherein the receiving coil is external and within a predetermined distance of the lossy housing;
wherein the receiving coil is a helical structure with a total rise that is less than or equal to a height of the lossy housing;
wherein the total rise is determined based on: (i) a first helical angle between a first turn and a second turn of the receiving coil; (ii) a second helical angle between a last turn and a second to last turn of the receiving coil; and (iii) a third helical angle between: (a) remaining turns between the second turn and the second to last turn, or (b) a majority of turns between the second turn and the second to last turn; and
wherein the first helical angle and the second helical angle are less than the third helical angle.

2. The medical device of claim 1, wherein the receiving coil comprises wound wire formed from conductive material, and the conductive material is comprised of gold (Au), gold/chromium (Au/Cr), platinum (Pt), platinum/iridium (Pt/Ir), titanium (Ti), gold/titanium (Au/Ti), or any alloy thereof.

3. The medical device of claim 1, wherein the predetermined distance is within 4 mm of the lossy housing, and the lossy housing is made of a material capable of causing attenuation or dissipation of the wireless power transfer signal.

4. A medical device comprising:
a housing;
power supply within the housing and connected to an electronics module; and
a receiving coil configured to exchange power wirelessly via a wireless power transfer signal and deliver the power to the power supply,
wherein the receiving coil is a helical structure with a height that is determined based on: (i) a first pitch between a first turn and a second turn of the receiving coil; (ii) a second pitch between a last turn and a second to last turn of the receiving coil; and (iii) a third pitch between: (a) remaining turns between the second turn and the second to last turn, or (b) a majority of turns between the second turn and the second to last turn, and
wherein the first pitch and the second pitch are less than the third pitch.

5. The medical device of claim 4, wherein the first pitch is the same as the second pitch.

6. The medical device of claim 4, wherein the helical structure has a shape of a rounded rectangle and includes from 4 to 15 turns.

7. The medical device of claim 4, wherein the height of the helical structure is less than or equal to a height of the lossy housing.

8. A neuromodulation system comprising:
a transmitting conductive structure configured to exchange power wirelessly via a wireless power transfer signal;
an implantable neurostimulator including:
   a lossy housing;
   a connector attached to a hole in the lossy housing;
   one or more feedthroughs that pass through the connector;
   an electronics module within the lossy housing and connected to the one or more feedthroughs;
   a power supply within the lossy housing and connected to the electronics module; and
   a receiving conductive structure disposed outside of the housing and connected to the power supply, wherein the receiving conductive structure is configured to exchange power wirelessly with the transmitting conductive structure via the wireless power transfer signal and deliver the power to the power supply,
   wherein the receiving conductive structure is external and within a predetermined distance of the lossy housing;
   wherein the receiving conductive structure is a helical structure with a total rise that is less than or equal to a height of the lossy housing;
   wherein the total rise is determined based on: (i) a first helical angle between a first turn and a second turn of the receiving conductive structure; (ii) a second helical angle between a last turn and a second to last turn of the receiving conductive structure; and (iii) a third helical angle between: (a) remaining turns between the second turn and the second to last turn, or (b) a majority of turns between the second turn and the second to last turn; and
   wherein the first helical angle and the second helical angle are less than the third helical angle, and
a lead assembly including:
   a lead body including a conductor material;
   a lead connector that connects the conductor material to the one or more feedthroughs; and
   one or more electrodes connected to the conductor material.

* * * * *